(12) United States Patent
Asada et al.

(10) Patent No.: US 6,399,565 B1
(45) Date of Patent: *Jun. 4, 2002

(54) THERAPEUTIC USE OF 20-KILODALTON HUMAN GROWTH HORMONE

(75) Inventors: Noriaki Asada; Miwa Ikeda; Masaru Honjo; Kazutoshi Horikomi; Takeshi Kamioka, all of Chiba (JP)

(73) Assignee: Schering Aktiengesellschaft (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/990,774

(22) Filed: Dec. 15, 1997

Related U.S. Application Data

(62) Division of application No. 08/668,469, filed on Jun. 25, 1996, now abandoned.

(30) Foreign Application Priority Data

Jun. 29, 1995 (JP) .............................. 7-163572
Dec. 5, 1995 (JP) .............................. 7-316883

(51) Int. Cl.⁷ ........................ A61K 38/27; A61K 38/00; C07K 14/00
(52) U.S. Cl. ............................... 514/2; 514/8; 514/12; 530/399
(58) Field of Search .................... 514/2, 8, 12; 530/399

(56) References Cited

U.S. PATENT DOCUMENTS 5,635,604 A   6/1997   Dalboge et al.

FOREIGN PATENT DOCUMENTS

EP   0 587 427 A1   3/1994
EP   0 735 140 A2   10/1996

OTHER PUBLICATIONS

Campbell et al. Proc. Soc. Exp. Biol. Med. 193(4): 269–273 (Abstract) Apr. 1990.*

Patent Abstracts of Japan, vol. 12, No. 312 (C–523), JP–A–63084500.

Culler et al., "Comparison of the acute metabolic effects of 22,000–dalton and 20, 000–dalton growth hormone in human subjects", Hormone and Metabolic Research, (Feb. 1988), 20(2) 107–109, XP002099021.

Campbell et al., "Lipolytic and antilipolytic effects of human growth hormone, its 20–kilodalton variant, a reduced and carboxymethylated derivative and human placental lactogen on chicken adipose tissue in vitro", Proceedings of the Society for Experimental Biology and Medicine (Apr. 1990), 193(4) 269–273, XP002099022.

Kostyo et al., "Biological characterization of purified native 20–kDa human growth hormone", Biochimica et biophsica Acta (Sep. 11, 1987) 925(3) 314–324, XP002099046.

Valk et al., "The effects of human growth hormone (GH) adminstration in GH–deficient adults: a 20–day metabolic ward study", J. Clinical Endocrinology & Metabolism, vol. 79, No. 4, Oct. 4, 1994, pp. 1070–1076, XP002099024.

Lewis ete al, *Endocrinol. Japan*, (Suppl. No. 1), 73–85, Apr. 1987.

Hisao Seo et al, *Igaku no Ayumi*, 165, 247–251, 1993.

Miyamoto et al, *International Symposium on GRF: Growth Hormone and Somatomedin Program and Abstracts*, 28, 1–2, 1986.

Fukashi Matsuzaki, *Igaku no Ayumi*, 165, 243–246, 1993.

Jorgensen et al, *European J. of Endocrinology*, 130, 224–228, 1994.

Bengtsson et al, *J. Clin. Endocrinol. Metab.*, 76, 309–317, 1993.

Beshyah et al, *Endocrinology and Metabolism*, (Suppl. B) 32, 1994.

Lewis et al, *J. Biol. Chem.*, 253, 2679–2687. 1978.

De Meytes et al, *J. Biol. Chem.*, 262, 11071–11079, 1987.

Lewis et al, *Biochem. Biophys. Res. Commun.*, 91, 778–782, 1979.

Lewis et al, *Metabolism*, 4, 237–243, 1985.

Shizume,"IGF–growth hormone and its related peptides", 132–136, 1992.

Sigel et al, *Endocrinology*, 108, 1600–1603, 1981.

Baumann et al, *Molecular and Cellular Endocrinology*, 73, 11–14, 1990.

Spencer et al, *Endocrinology*, Voo. 109, No. 4, 1901–1302, 1981.

Martial et al, *Science*, 205–602–607, 1979.

Masuda et al, *Biophysica Acta*, 949, 125–131, 1988.

Biochim. Biophys. Acta., 925:314–324 (1987).

Smal et al. Biochem. Biophys. Res. Comm. 134(1): 159–195, 1986.*

* cited by examiner

*Primary Examiner*—Elizabeth C. Kemmerer
*Assistant Examiner*—Regina M. DeBerry
(74) *Attorney, Agent, or Firm*—Burns, Doane, Swecker & Mathis, LLP

(57) ABSTRACT

Administration of an administrative amount of an authentic human growth hormone having a molecular weight of 20,000 daltons to human adults can improve body composition, stimulate lipolysis, increase serum insulin-like growth factor I or be used in replacement therapy for human growth hormone-deficient patients.

31 Claims, 6 Drawing Sheets

Stimulation of lipolytic activity of authentic 20-kilodalton human growth hormone and 22-kilodalton human growth hormone in mouse 3T3-L1 adipocytes.

Stimulation of lipolytic activity of authentic 20-kilodalton human growth hormone and 22-kilodalton human growth hormone in rat epididymal adipose tissues.

Stimulation of lipolytic activity of authentic 20-kilodalton human growth hormone and 22-kilodalton human growth hormone in hypophysectomized rats.

Effect of authentic 20-kilodalton human growth hormone and 22-kilodalton human growth hormone on improvement of body composition in C57BL/6j-ob/ob mice.

Effect of authentic 20-kilodalton human growth hormone and 22-kilodalton human growth hormone on serum IGF-I concentration in hypophysectomized rats.

THERAPEUTIC USE OF 20-KILODALTON HUMAN GROWTH HORMONE

This application is a divisional, of application Ser. No. 08/668,469 filed Jun. 25, 1996, now abandoned.

BACKGROUND OF THE INVENTION

1. Field of the Invention

The present invention relates to a human growth hormone agent for adults, more specifically to a human growth hormone agent for replacement therapy for growth hormone-deficient adult patients.

2. Description of the Related Art

A human growth hormone is a hormone which is continuously secreted from the pituitary gland not only during a growth period but also all through life in a normal human. The human growth hormone was first extracted and purified from the human pituitary gland. The human growth hormone has known to exist in two types: one having a molecular weight of about 22,000 (hereinafter referred to as 22-kilodalton human growth hormone) and the other having a molecular weight of about 20,000 (hereinafter referred to as 20-kilodalton human growth hormone). It has been reported that the 20-kilodalton human growth hormone has a growth promoting activity equivalent to that of the 22-kilodalton human growth hormone but has a weaker activity in inducing glucose intolerance than the 22-kilodalton human growth hormone so that it may be less diabetogenic (Lewis U. J., et al: Endocrinol. Japan 34 73–85, 1987). Accordingly, effectiveness of the 20-kilodalton human growth hormone as a therapeutic agent for growth hormone deficiency has attracted attention (Hisao Seo, et al: Igaku no Ayumi 165 247–251, 1993).

However, in spite of the development in recombinant DNA technology, production of the 20-kilodalton human growth hormone was extremely difficult and the amount of expression of the 20-kilodalton human growth hormone having an additional Met at the N-terminal in an intracellular expression method was 1/20 that of the 22-kilodalton human growth hormone (Miyamoto, et al: International Symposium on GRF; Growth Hormone and Somatomedin Program and Abstracts 28 1–2, 1986). In manufacturing proteins, it is known that generally, higher-order structures in the cells are not properly formed in the intracellular expression method, so that a refolding process is required. However, since unlike the 22-kilodalton human growth hormone, there is no international standard product for this 20-kilodalton human growth hormone, it is difficult to evaluate the appropriateness of the structure attained by the refolding process by comparison with a standard product. Furthermore, this 20-kilodalton human growth hormone is highly hydrophobic, which makes purification process difficult and substantially defies a secretion method for the production of an authentic 20-kilodalton human growth hormone having the amino acid sequence identical to that of the 20-kilodalton human growth hormone derived from the pituitary gland.

Thus, such a poor availability of the authentic 20-kilodalton human growth hormone has been an obstacle to study its potentiality as a medicament (Fukashi Matsuzaki: Igaku no Ayumi 165 243–246, 1993).

Biological properties of the human growth hormone, which are the foundation of its potentiality as a medicament, will be described as follows:

A growth hormone is associated with various events in the body, such as lipolysis, protein anabolism and osteogenesis. Therefore, in growth hormone-deficient patients, a lipolytic activity, an insulin-like growth factor I (hereinafter referred to as IGF-I) secreting activity, a protein synthesis stimulating activity, a bone metabolizing activity or the like are being decreased. Among them, the decrease in lipolytic activity is one of the factors to cause accumulation of subcutaneous fat or visceral fat, which results in marked obesity. Thus, in growth hormone-deficient patients, a complication with hyperlipemia is known to occur in many cases and the morbidity in circulatory disorders such as arteriosclerosis and the mortality from cardiovascular diseases are reported to be high. It has also been reported that since IGF-I is associated with various physiological events in the body, the decrease in the serum IGF-I concentration due to the reduced IGF-I secreting activity causes various disorders. Furthermore, it has also been reported that the decrease in the protein synthesis stimulating activity causes a decrease in muscular strength and exercise capacity, which may cause problems in daily activities.

From the fact described above, in growth hormone-deficient patients, it is required to improve body composition, namely to bring body protein content, body fat content and bone density close to normal levels. More specifically, it is required to increase a decreased body protein content and bone density and to decrease an increased body fat content. To decrease the body fat content here implies suppression of body fat accumulation, stimulation of body fat hydrolysis and the like so that the stimulation of body fat hydrolysis is not the only cause of the decrease in the body fat content. Therefore, the stimulation of body fat hydrolysis is one of the factors to improve the body composition.

Some activities related to the 22-kilodalton human growth hormone in growth hormone-deficient patients are conventionally known as follows:

As a replacement therapy for growth hormone-deficient patients, administrations of the 22-kilodalton human growth hormone produced by a recombinant DNA technique to the patients have been tried; with regard to the above-mentioned improvement of the body composition, it was reported that an administration of the 22-kilodalton human growth hormone over a period of 3 years reduced the body fat content to normal level (Jorgensen, J. OL., et al: European Journal of Endocrinology 130 224–228, 1994) and an administration of the 22-kilodalton human growth hormone over a period of 6 weeks increased the serum IGF-I concentration to a normal level, and improved the body nitrogen level, which implies the body protein level, bringing it close to normal (Bengtsson, B. A., et al: J. Clin. Endocrinol. Metab. 76 309–317, 1993). However, with regard to adults other than growth hormone-deficient patients, no knowledge is available since no administrative experiment has been conducted.

On the other hand, there is concern that the administration of human growth hormones to adults tends to induce glucose intolerance. In fact, it was indicated that the administration to growth hormone-deficient adult patients induced not frequent but serious abnormalities in glucose metabolism (Beshyah, S. A., et al: Endocrinology and Metabolism (suppl. B), 32, 1994).

It has been difficult to obtain the authentic 20-kilodalton human growth hormone. As a result, in most experimental studies regarding physiological properties of the 20-kilodalton human growth hormone to date, either a purified product prepared from the pituitary gland or a non-authentic recombinant product having a methionine at the N-terminal (hereinafter referred to as Met-type 20-kilodalton human growth hormone) which is prepared by a recombinant gene technique, had been used. Physiological properties obtained from the experiments using these products are described as follows:

A growth promoting activity of the 20-kilodalton human growth hormone, which was extracted and purified from the pituitary gland, was reported to be the same as that of the 22-kilodalton human growth hormone (Lewis, U. J., et al: J. Biol. Chem. 253 2679–2687, 1978). As to affinity to adipocytes and lipolysis stimulating activity, the following is known. The affinity of the 20-kilodalton human growth hormone, which is extracted and purified from the pituitary gland, to adipocytes is as markedly low as 3% of that of the 22-kilodalton human growth hormone (De Meyts, P., et al: J. Biol. Chem. 262 11071–11079, 1987). On the other hand, as to the lipolysis stimulating activity, which is important in the administration to growth hormone-deficient adult patients, a serum free fatty acid concentration was increased by 40% due to the lipolysis stimulation in vivo with the 22-kilodalton human growth hormone, while no increase was observed with the 20-kilodalton human growth hormone which was extracted and purified from the pituitary gland (Lewis, U. J., et al: Biochem. Biophys. Res. Commun. 91 778–782, 1979). Furthermore, the 20-kilodalton human growth hormone, which was extracted and purified from the pituitary gland, had no lipolysis stimulating activity in vitro (Lewis, U. J., et al: Metabolism 4 237–243, 1985).

Thus, the 20-kilodalton human growth hormone was conventionally considered to have no or reduced lipolysis stimulating activity as compared to the 22-kilodalton human growth hormone. This fact defies anticipation that the 20-kilodalton human growth hormone might have an advantage which is expected from its low potential to induce glucose intolerance in the administration to adults, particularly to growth hormone-deficient adult patients and thus possibly denies its effectiveness in the above-mentioned lipolysis stimulation and body composition improvement in the administration to the growth hormone-deficient adult patients.

As to the serum IGF-I concentration increasing activity, the following is known. The serum IGF-I is known to be released primarily from the liver by binding of growth hormones to liver receptors ("IGF-growth hormone and its related peptides" by Kazuo Shizume, 132–136, 1992); however, the affinity of the 20-kilodalton human growth hormone, which is extracted and purified from the pituitary gland, to the liver receptors is known to be 3–12% in rats and 8–20% in rabbits of that of the 22-kilodalton human growth hormone, respectively (Sigel, M. B., et al: Endocrinology 108 1600–1603, 1981); in humans, the affinity to the liver receptors is known to be almost none with the 20-kilodalton human growth hormone, which is extracted and purified from the pituitary gland, and with the Met-type 20-kilodalton human growth hormone (Baumann, G., et al: Molecular and Cellular Endocrinology 73 11–14, 1990).

Accordingly, it was suggested that the 20-kilodalton human growth hormone has none or low activity for IGF-I producing in the liver and releasing from the liver. Yet, there was a report that the 20-kilodalton human growth hormone, which was extracted and purified from the pituitary gland, brought a serum IGF-I concentration similar to that with the 22-kilodalton human growth hormone, when administered to hypophysectomized rats (Spencer, E., et al: Endocrinol. 101 1301–1302, 1981). However, it was pointed out that in purifying the 20-kilodalton human growth hormone from the pituitary gland, a complete separation of the 20-kilodalton human growth hormone from the 22-kilodalton human growth hormone is difficult because of their similarity in physicochemical properties and therefore the 20-kilodalton human growth hormone, which is extracted and purified from the pituitary gland, used for experiments to date was mixed with the 22-kilodalton human growth hormone, which might have affected results of the experiments (Baumann, G., et al: Molecular and Cellular Endocrinology 73 11–14, 1990). Consequently, sufficient knowledge on the basis of studies using a pure 20-kilodalton human growth hormone has not been attained.

SUMMARY OF THE INVENTION

As mentioned above, as to the authentic 20-kilodalton human growth hormone, almost no knowledge had been attained in regard to its activity in improving the body composition, stimulating lipolysis or increasing the serum IGF-I concentration.

The subject of the present invention is to solve the problem in providing a human growth hormone agent for adults, which is effective in improving the body composition, stimulating lipolysis and/or increasing the serum IGF-I concentration and accordingly, an object of the present invention is to provide a human growth hormone agent for replacement therapy for adults, particularly for growth hormone-deficient adult patients, which contains an authentic 20-kilodalton human growth hormone as an active component and has a low activity in inducing glucose intolerance.

In order to solve the above-mentioned problem, the present inventors established a process for the production of an authentic 20-kilodalton human growth hormone by a recombinant DNA technique, prepared a pharmaceutical preparation containing the authentic 20-kilodalton human growth hormone and conducted various studies using the resultant human growth hormone agent. As a result, the present inventors novelly found that the authentic 20-kilodalton human growth hormone has significant activities in improving the body composition, stimulating lipolysis and/or increasing the serum IGF-I concentration and furthermore reconfirmed that the authentic 20-kilodalton human growth hormone is less diabetogenic than the 22-kilodalton human growth hormone.

The above-mentioned knowledge on the authentic 20-kilodalton human growth hormone thus obtained could not be predicted from the conventional knowledge on the 20-kilodalton human growth hormone, which is extracted and purified from the pituitary gland, or the Met-type 20-kilodalton human growth hormone. Namely, the knowledge that the authentic 20-kilodalton human growth hormone has the activity to stimulate lipolysis, which is one of the factors to improve the body composition, could not be predicted from results of experiments using the 20-kilodalton human growth hormone which was extracted and purified from the pituitary gland. Furthermore, the knowledge that the pure authentic 20-kilodalton human growth hormone without a 22-kilodalton human growth hormone has the capability to increase the serum IGF-I concentration as did the 22-kilodalton human growth hormone could not be readily predicted from the conventional knowledge that the 20-kilodalton human growth hormone has a low affinity to the liver receptors (Baumann, G., et al: Molecular and Cellular Endocrinology 73 11–14, 1990). The present inventors have now found that the above-mentioned authentic 20-kilodalton human growth hormone has significant activities in improving the body composition, stimulating lipolysis and increasing the serum IGF-I concentration so that the usefulness of the 20-kilodalton human growth hormone as a medicament for adults is confirmed.

The present inventors found that the authentic 20-kilodalton human growth hormone has excellent capabilities in improving the body composition, stimulating lipolysis and increasing the serum IGF-I concentration, contrary to the conventional knowledge so far reported on the 20-kilodalton human growth hormone.

From the knowledge mentioned above, this agent can be used as a human growth hormone agent for adults, particularly as an excellent human growth hormone agent in replacement therapy for growth hormone-deficient adult patients.

DETAILED DESCRIPTION OF THE PREFERRED EMBODIMENTS

Figure 1:
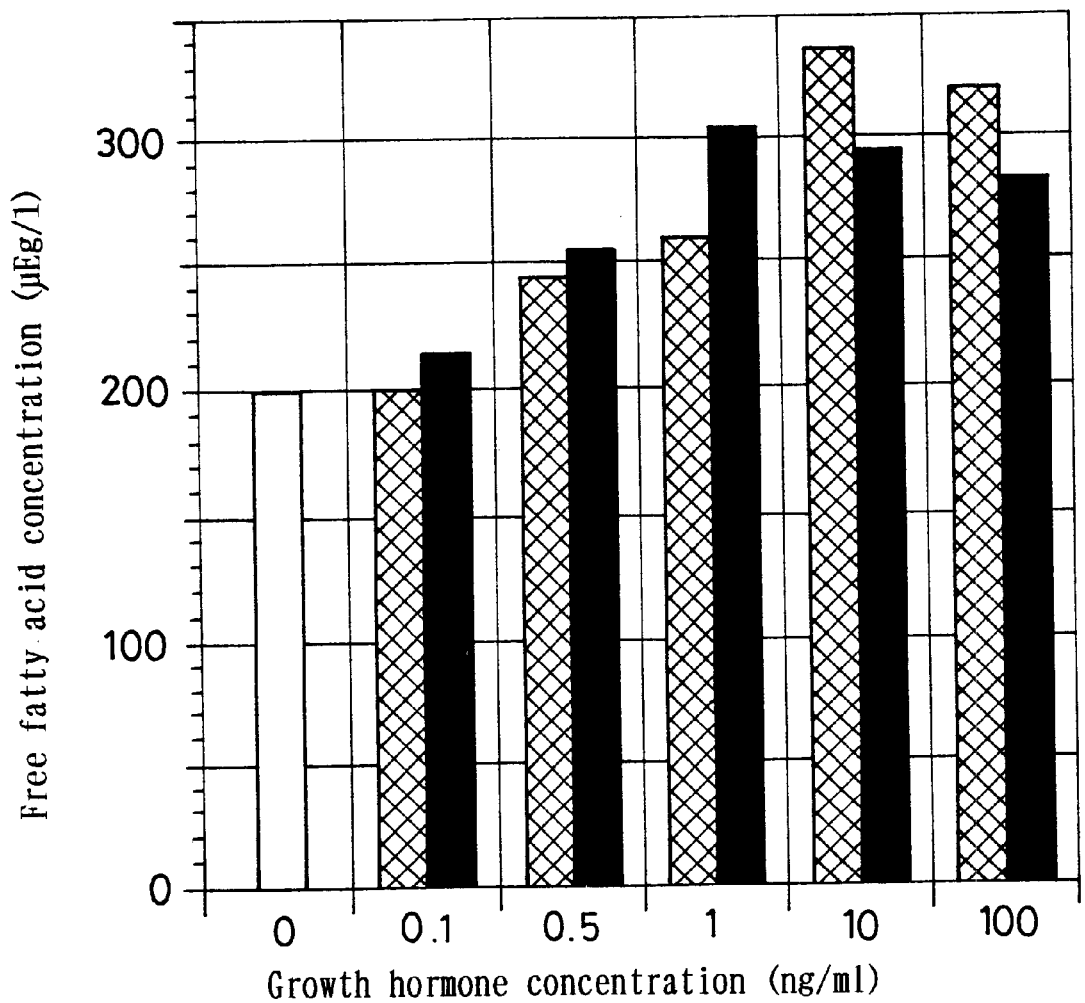
FIG. 1 illustrates stimulation of lipolytic activity of human growth hormones in mouse 3T3-L1 adipocytes. Open column: without growth hormones; crisscross-patterned column: with 22-kilodalton human growth hormone; and solid column: with authentic 20-kilodalton human growth hormone.

The present invention provides a human growth hormone agent for adults, which contains an authentic 20-kilodalton human growth hormone as an effective component.

The human growth hormone agent for adults contains the authentic 20-kilodalton human growth hormone as a major component.

The authentic 20-kilodalton human growth hormone implies a human growth hormone which has a molecular weight of about 20,000 and does not have Met attached to the N-terminal. As for the authentic 20-kilodalton human growth hormone, two types have been reported, in which the 14th amino acid from the N-terminal is Met and Ser, respectively, SEQ ID NO: 1 and SEQ ID NO: 2, respectively. Namely, Martial et al (Martial, J. A., et al: Science 205 602, 1979) reported that mRNA sequence coding for the 14th amino acid from the N-terminal was AUG (coding for Met) and Masuda et al (Masuda, N., et al: Biophysica Acta 949 125, 1988) reported that the cDNA sequence coding for the 14th amino acid from the N-terminal was AGT (coding for Ser). Amino acid sequences of these two types are as follows:

```
SEQ ID NO: 1:

Phe Pro Thr Ile Pro Leu Ser Arg Leu Phe Asp Asn Ala Met Leu
 1               5                  10                  15

Arg Ala His Arg Leu His Gln Leu Ala Phe Asp Thr Tyr Gln Glu
                20                  25                  30

Phe Asn Pro Gln Thr Ser Leu Cys Phe Ser Glu Ser Ile Pro Thr
                35                  40                  45

Pro Ser Asn Arg Glu Glu Thr Gln Gln Lys Ser Asn Leu Glu Leu
                50                  55                  60

Leu Arg Ile Ser Leu Leu Leu Ile Gln Ser Trp Leu Glu Pro Val
                65                  70                  75

Gln Phe Leu Arg Ser Val Phe Ala Asn Ser Leu Val Tyr Gly Ala
                80                  85                  90

Ser Asp Ser Asn Val Tyr Asp Leu Leu Lys Asp Leu Glu Glu Gly
                95                  100                 105

Ile Gln Thr Leu Met Gly Arg Leu Glu Asp Gly Ser Pro Arg Thr
                110                 115                 120

Gly Gln Ile Phe Lys Gln Thr Tyr Ser Lys PHe Asp Thr Asn Ser
                125                 130                 135

His Asn Asp Asp Ala Leu Leu Lys Asn Tyr Gly Leu Leu Tyr Cys
                140                 145                 150
```

-continued

```
Phe Arg Lys Asp Met Asp Lys Val Glu Thr Phe Leu Arg Ile Val
                155             160                 165

Gln Cys Arg Ser Val Glu Gly Ser Cys Gly Phe
                170             175

SEQ ID NO: 2:

Phe Pro Thr Ile Pro Leu Ser Arg Leu Phe Asp Asn Ala Ser Leu
 1               5               10                  15

Arg Ala His Arg Leu His Gln Leu Ala Phe Asp Thr Tyr Gln Glu
                20              25                  30

Phe Asn Pro Gln Thr Ser Leu Cys Phe Ser Glu Ser Ile Pro Thr
                35              40                  45

Pro Ser Asn Arg Glu Glu Thr Gln Gln Lys Ser Asn Leu Glu Leu
                50              55                  60

Leu Arg Ile Ser Leu Leu Leu Ile Gln Ser Trp Leu Glu Pro Val
                65              70                  75

Gln Phe Leu Arg Ser Val Phe Ala Asn Ser Leu Val Tyr Gly Ala
                80              85                  90

Ser Asp Ser Asn Val Tyr Asp Leu Leu Lys Asp Leu Glu Glu Gly
                95              100                 105

Ile Gln Thr Leu Met Gly Arg Leu Glu Asp Gly Ser Pro Arg Thr
                110             115                 120

Gly Gln Ile PHe Lys Gln Thr Tyr Ser Lys Phe Asp Thr Asn Ser
                125             130                 135

His Asn Asp Asp Ala Leu Leu Lys Asn Tyr Gly Leu Leu Tyr Cys
                140             145                 150

Phe Arg Lys Asp Met Asp Lys Val Glu Thr Phe Leu Arg Ile Val
                155             160                 165

Gln Cys Arg Ser Val Glu Gly Ser Cys Gly Phe
                170             175
```

Both types can be used in the hormone agent according to the present invention. Furthermore, amino acid sequences in which one or two amino acids are replaced, lacked, inserted or deleted should be understood to fall under the category of the authentic 20-kilodalton human growth hormone according to the present invention.

In preparing a pharmaceutical preparation of the present invention, an additive which is customarily used in pharmaceutical preparations, a medically acceptable solvent or the like may be used.

The pharmaceutical composition of the present invention can be prepared by combining the authentic 20-kilodalton human growth hormone with a pharmaceutically acceptable carrier or diluent. An effective amount of the authentic 20-kilodalton human growth hormone, for example, 0.1–99 wt. %, preferably 0.5–20% of the authentic 20-kilodalton human growth hormone may be contained in the pharmaceutical composition of the present invention.

The medical composition of the present invention may be supplied in the frozen or freeze-dried form with a suitable carrier and/or diluent.

The medical composition of the present invention may be administered according to the conventional manner in the treatment using growth hormone. For example, it may be administered by hypodermic injection or intramuscular injection.

Any carriers and diluents used in the conventional manners may be also used. For example, an aqueous injection can be prepared by adding the effective component to water for injection, optionally with a suitable additive(s).

Doses of the authentic 20-kilodalton human growth hormone for human adults may vary, case by case. For example, a dose of 0.005–5 mg, preferably 0.015–1.5 mg of the authentic 20-kilodalton human growth hormone per 1 kg of body weight may be repeated several times in a week.

EXAMPLES

The present invention will be explained in detail by the following examples; however, the invention is not intended to be limited to these examples.

Example 1

Production of Authentic 20-kilodalton Human Growth Hormone

*Escherichia coli* transformant MT-10765 (this strain was deposited with an accession number of FERM BP-5020 at the National Institute of Bioscience and Human-Technology of the Agency of Industrial Science & Technology of the Ministry of International Trade and Industry 1-3, Higashi 1-chome, Tukuba-shi, Ibaraki-ken, 305, Japan in accordance with the Budapest Treaty) were inoculated in a 2-fold concentrated LB medium containing 0.5% glycerol and cgultured at 28° C. for 20 hours. After cultivation, the cells were collected and the periplasm fraction in solution which contained an authentic 20-kilodalton human growth hormone was obtained by an osmotic shock procedure. The fraction was purified by ion exchange chromatography and gel-filtration chromatography and the resulting authentic 20-kilodalton human growth hormone having the amino acid sequence of SEQ ID NO:1 was dissolved in a phosphate buffer solution. Its purity was 99.9% as analyzed by reverse-phase HPLC and SDS-PAGE. It was stored frozen.

Example 2
Production of Human Growth Hormone Agent for Replacement Therapy for Adults.

2.4 mg of D-mannitol was added to 1.4 mg of the authentic 20-kilodalton human growth hormone obtained in Example 1. The admixture was stored frozen and used for manufacturing a growth hormone agent for replacement therapy for adults.

Example 3
Study on Lipolysis Stimulating Activity of Authentic 20-kilodalton Human Growth Hormone in Mouse 3T3-L1 Adipocytes Dulbecco's Modified Eagle Medium (DMEM) containing 10% calf serum was dispensed into wells of a 24-well multi-well plate. Mouse 3T3-L1 fibroblasts (Dainippon Pharmaceutical Co., Ltd.) were seeded into the wells and incubated until confluent and then further for 2 days. The day when the incubation was completed was set as day 0 of differentiation induction. The medium was replaced by a differentiation induction medium, namely DMEM containing 10% fetal calf serum (FCS), 0.5 mM 3-isobutyl-1-methylxanthine, 0.25 $\mu$M dexamethasone, 172 nM insulin and incubation was continued. The medium was replaced by DMEM containing 10% FCS and 172 nM insulin on day 2 of differentiation induction and then by DMEM containing 10% FCS on day 4 of differentiation induction. On day 6 or 7 of differentiation induction, the medium was replaced by the same medium as used on day 4 of differentiation induction to convert the mouse 3T3-L1 fibroblasts to adipocytes. In the culture mentioned above, 50 U of penicillin and 50 $\mu$g/ml of streptomycin were added to all media to prevent contamination and the incubation was carried out at 37° C. under a 5% $CO_2$ atmosphere.

On day 8 or day 9 of differentiation induction when the fiblobrasts were sufficiently converted to adipocytes, the medium was replaced by DMEM containing 2% bovine serum albumin (BSA) in order to remove an effect of serum. The cultivation was then continued for 24 hours.

The medium of adipocytes thus obtained was removed and 750 $\mu$l/well of a Krebs-Ringer buffer solution (1.2 mM $KH_2PO_4$, 4.7 mM KCl, 118 mM NaCl, 25 mM $NaHCO_3$, 2.5 mM $CaCl_2$, pH 7.4) containing 4% BSA, 2 mM glucose and 40 nM dexamethasone was dispensed into the wells of a multi-well plate. The authentic 20-kilodalton human growth hormone prepared in Example 1 or 22-kilodalton human growth hormone (Genotropin, Sumitomo Pharmaceutical Co., Ltd.) were added at concentrations of 0, 0.1, 0.5, 1, 10, 100 ng/ml to the wells thus prepared, then incubated at 37° C. for 48 hours under a 5% $CO_2$ atmosphere.

The amount of free fatty acids released into the incubation medium, which is one of the indices for lipolysis, was measured with NEFA C-Test Wako (Wako Pure Chemical Industries Ltd.).

This lipolysis stimulation experiment was conducted in quadruplicate for each concentration of growth hormones. The measured figures were calculated in terms of oleic acid equivalent.

Results are shown in FIG. 1. The authentic 20-kilodalton human growth hormone showed a significant lipolysis stimulating activity at a concentration at or higher than 0.5 ng/ml, and a lipolysis stimulating activity equivalent to or higher than the 22-kilodalton human growth hormone at a concentration which is clinically significant as a replacement therapy for adults, particularly for growth hormone-deficient adult patients.

Example 4
Study on Lipolysis Stimulating Activity of Authentic 20-kilodalton Human Growth Hormone in Adipose Tissues Derived from Rat Epididymal Fat.

6-week-old male Slc:SD rats were euthanised and adipose tissues derived from the epididymal fat were excised from the animals. 10 ml of a Krebs-Ringer buffer solution containing 4% BSA, 255 nM dexamethasone, 5.5 mM glucose (pH 7.4) were dispensed into a 100 mm-diameter dish, and 15 pieces of the excised tissue segments, each weighing 30–50 mg, were added to each dish each. The authentic 20-kilodalton human growth hormone produced in Example 1, or the 22-kilodalton human growth hormone (Genotropin, Sumitomo Pharmaceutical Co., Ltd.) were at concentrations of 0, 1, 10, 100, 1000 and 2500 ng/ml to the dishes thus prepared, then incubated at 37° C. for 4 hours under a 5% $CO_2$ atmosphere. After this preincubation, 1 ml each of fresh medium of the identical composition as used in the preincubation was dispensed into each well of a 24-well multi-well plate, one piece of tissue fragment was transferred to each well. Incubation was then carried out for 5 hours under the same conditions as in the preincubation.

The amount of glycerol released into the incubation medium, which is one of the indices for lipolysis, was measured with F-kit glycerol (Boehringer Mannheim).

This lipolysis stimulation experiment was conducted using 15 segments for each concentration of growth hormones. The measurements were expressed as a molar concentration per each adipose tissue fragment by weight.

Figure 2:
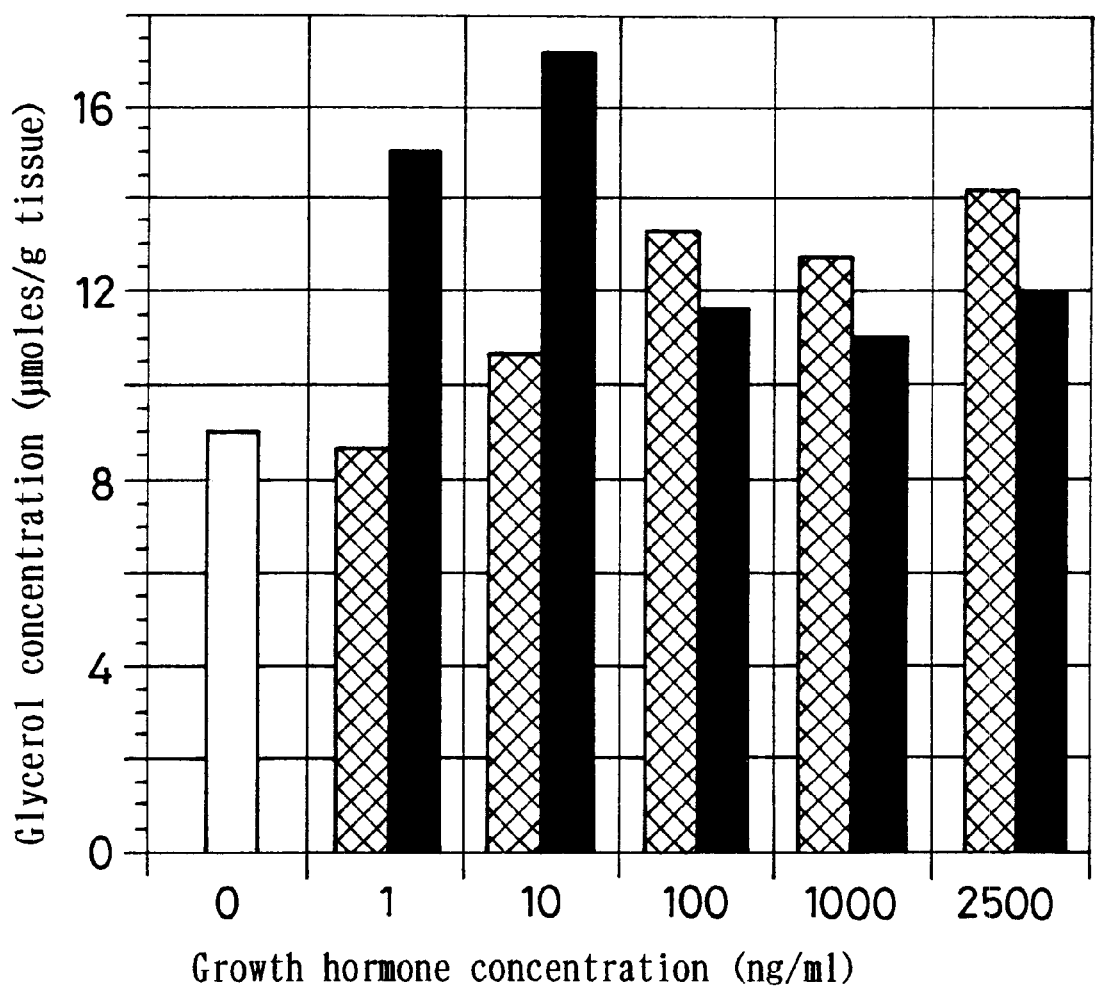
FIG. 2 illustrates stimulation of lipolytic activity of human growth hormones in adipose tissues derived from rat epididymal fat. Open column: without growth hormones; crisscross-patterned column: with 22-kilodalton human growth hormone; and solid column: with authentic 20-kilodalton human growth hormone.

Results are shown in FIG. 2. The authentic 20-kilodalton human growth hormone showed a significant lipolysis stimulating activity at a concentration at or higher than 1 ng/ml, and a lipolysis stimulating activity equivalent to or higher than the 22-kilodalton human growth hormone at a concentration which is clinically significant as a replacement therapy for adults, particularly for growth hormone-deficient adult patients.

Example 5
Study on Lipolysis Stimulating Activity of Authentic 20-kilodalton Human Growth Hormone in Hypophysectomized Rats 4-week-old male Slc:SD rats were hypophysectomized, fed until 6 weeks old, then fasted overnight. The authentic 20-kilodalton human growth hormone produced in Example 1 or the 22-kilodalton human growth hormone (Genotropin, Sumitomo Pharmaceutical Co., Ltd.) were administered intraperitoneally to these animals at 50 or 100 $\mu$g per rat. Saline was administered in place of the growth hormones to control animals. Blood was taken from the jugular vein 5 hours after the administration of the growth hormones (or saline), and the serum free fatty acid concentration was measured using NEFA C-Test Wako (Wako Pure Chemical Industries Ltd.).

This experiment was conducted using 6 hypophysectomized rats in each group. The measurements were calculated in terms of oleic acid equivalent.

Figure 3:
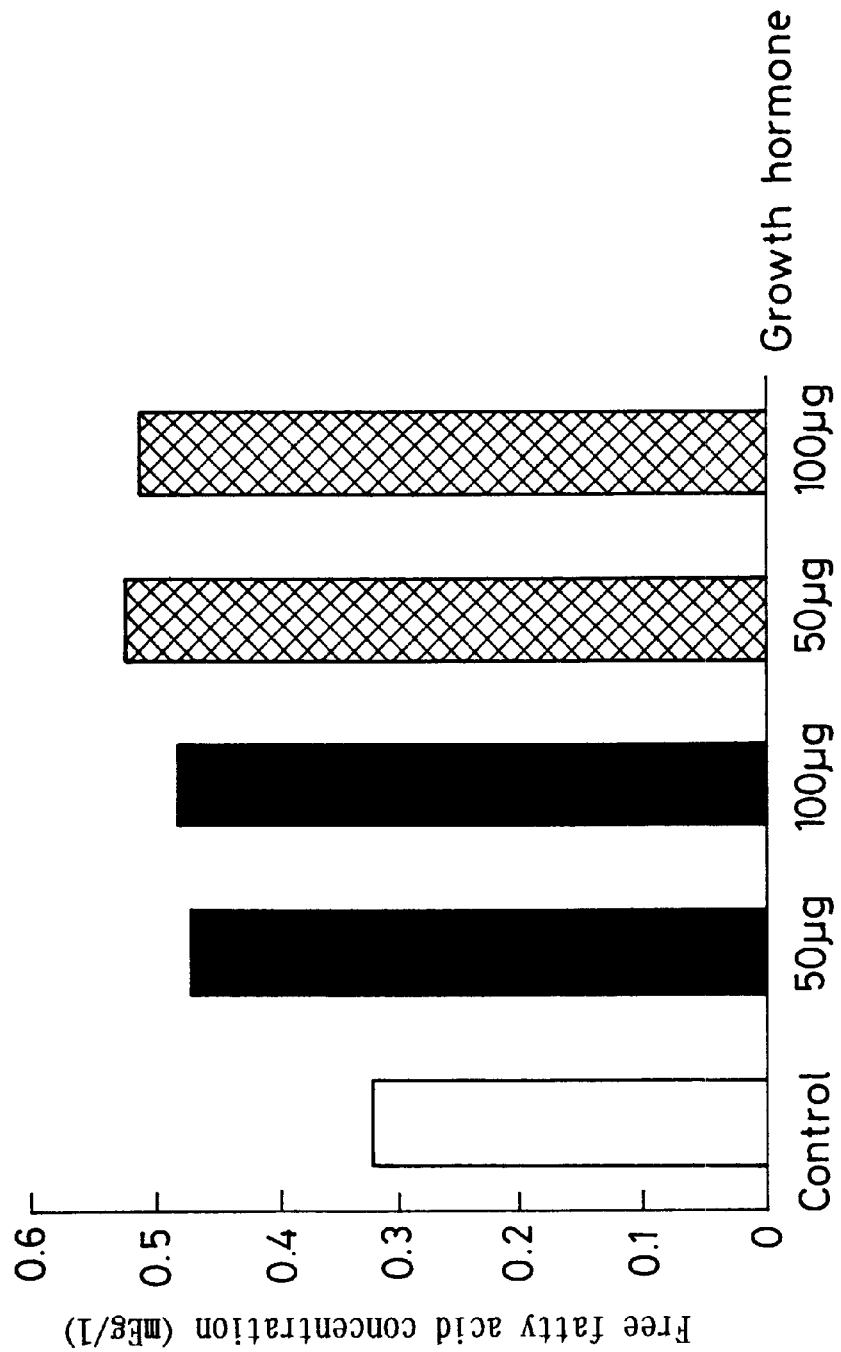
FIG. 3 illustrates stimulation of lipolytic activity of human growth hormones in hypophysectomized rats. Open column: control; crisscross-patterned column: with 22-kilodalton human growth hormone; and solid column: with authentic 20-kilodalton human growth hormone.

Results are shown in FIG. 3. The administration of the authentic 20-kilodalton human growth hormone showed a significant increase in the serum free fatty acid concentration, which was caused by body fat hydrolysis, as did the administration of 22-kilodalton human growth hormone. Thus, it was demonstrated that the authentic 20-kilodalton human growth hormone has a lipolysis stimulating activity, which is necessary for the replacement therapy for adults, particularly growth hormone-deficient adult patients, equal that of the 22-kilodalton human growth hormone, substantially in vivo.

Example 6

Study on Body Composition Improving Activity of Authentic 20-kilodalton Human Growth Hormone in C57BL/6J-ob/ob Mice 6-week-old female C57BL/6J-ob/ob mice were subcutaneously injected in the back with the authentic 20-kilodalton human growth hormone produced in Example 1 or the 22-kilodalton human growth hormone (Genotropin, Sumitomo Pharmaceutical Co., Ltd.,) at a dosage of 500 μg/mouse/day for 10 days. Saline was administered to control animals. On the last day of the experiment, after measuring body weights, each animal was euthanised, freeze-dried, then homogenized with water to obtain 200 ml total of homogenate. The following measurements were carried out using this homogenate.

1. Measurement of body water content

A portion of the above-mentioned homogenate was freeze-dried, from which its dry weight was obtained and the total dry body weight was extrapolated from this measurement. Body water content of each animal was calculated from the difference between the body weight previously obtained and the dry body weight thus obtained.

2. Measurement of body protein 1 ml of the above-mentioned homogenate was diluted 100 times with a 1 N NaOH solution, and the resultant suspension was neutralized with a 1 N HCl solution. To remove the fat, 1 ml of this suspension was admixed with 1 ml of $CHCl_3$ for 10 minutes and the mixture was allowed to stand for 10 minutes to obtain a water layer free of fat. The protein content of this water layer was measured by the Lowry method using a BSA standard and total body protein was calculated from the resulting measurements.

3. Measurement of fat

200 μl of a 250 mg/ml KCl solution and 7.5 ml of methanol were added to 5 ml of the above-mentioned homogenate and the mixture was shaked. Then, 3.75 ml of $CHCl_3$ was added and the mixture was shaked for 10 minutes using a shaker. The mixture was allowed to stand for 10 minutes and then shaked for 30 seconds with an addition of 3.75 ml of $CHCl_3$ and then further shaked for 30 seconds with an addition of 3.75 ml of a 20 mg/ml KCl solution. The resulting mixture was centrifuged at 3000 g for 10 minutes, then the $CHCl_3$ layer was taken into a screw top test tube and concentrated at 40° C. under a nitrogen gas flow. Next, a $CHCl_3$:methanol (=2:1) solution was added to make the mixture 8 ml, 1.6 ml of an 8.8 mg/ml KCl solution was added, and the resulting mixture was shaked for 10 minutes. The mixture was then centrifuged at 3000 g for 10 minutes, after which the $CHCl_3$ layer was removed into a weighed glass test tube, and concentrated under a nitrogen gas flow to measure the fat content. The fat content of the whole body was calculated from this measurement.

The results showed the same increase in body protein with both the authentic 20-kilodalton. human growth hormone and the 22-kilodalton human growth hormone.

Furthermore, the body water, body protein and body fat contents obtained by the measurements above were totalled, and % body fat of the total body was calculated. The values before and after the administration of growth hormones were compared.

The experiment was conducted using 7 mice in each group.

Figure 4:
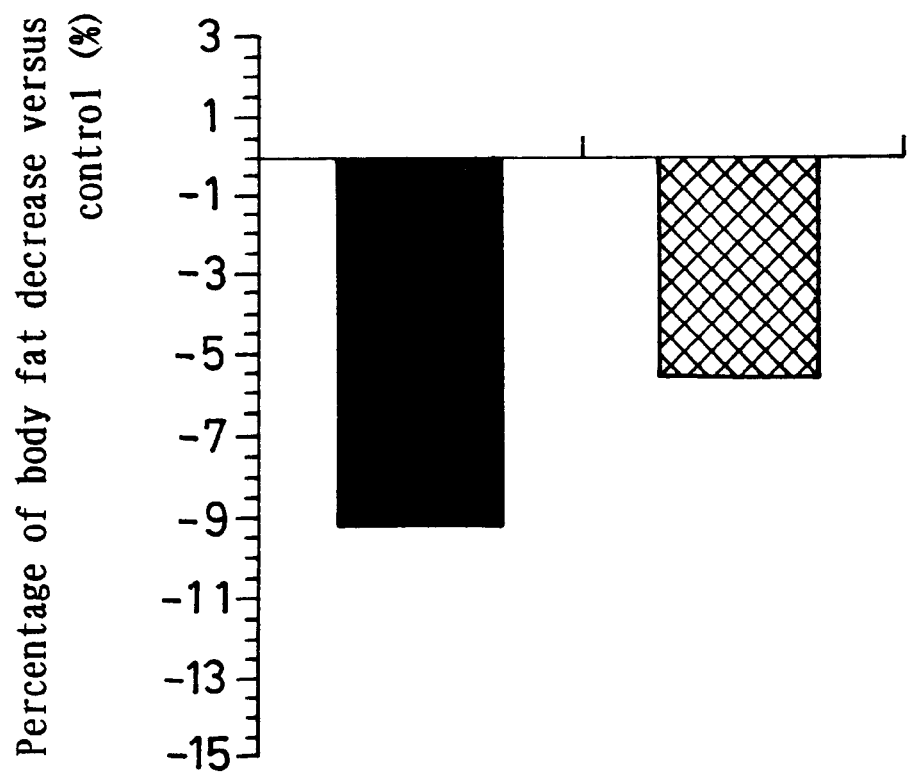
FIG. 4 illustrates a body composition improving activity of human growth hormones in C57BL/6J-ob/ob mice. Crisscrossed column: with 22-kilodalton human growth hormone; and solid column: with authentic 20-kilodalton human growth hormone.

Results are shown in FIG. 4. It was demonstrated that the authentic 20-kilodalton human growth hormone had a body fat reduction stimulating activity equal to or higher than that of the 22-kilodalton human growth hormone, indicating that the authentic 20-kilodalton human growth hormone has a significant body composition improving activity equal to or higher than that of the 22-kilodalton human growth hormone. These results showed that the authentic 20-kilodalton human growth hormone had a body composition improving activity, which is necessary for replacement therapy for adults, particularly growth hormone-deficient adult patients, equal to that of the 22-kilodalton human growth hormone.

Example 7

Study on Serum IGF-I Concentration Increasing Activity of Authentic 20-kilodalton Human Growth Hormone in Hypophysectomized Rats 4-week-old male Slc:SD rats were hypophysectomized and the animals were fed until 6 weeks old, then injected with 10 or 50 μg/rat/day of the authentic 20-kilodalton human growth hormone produced in Example 1 or the 22-kilodalton human growth hormone (Genotropin, Sumitomo Pharmaceuticals Co., Ltd.) subcutaneously in the back of the neck for 10 days. Saline was administered to control animals. Blood was taken from the dorsal vein 3 hours after the final administration of the growth hormones (or saline) and the serum IGF-I level was measured with Somatomedin-C EIKEN II (Eiken Chemical Co., Ltd.).

The experiment was conducted using 6 hypophysectomized rats in each group.

Figure 5:
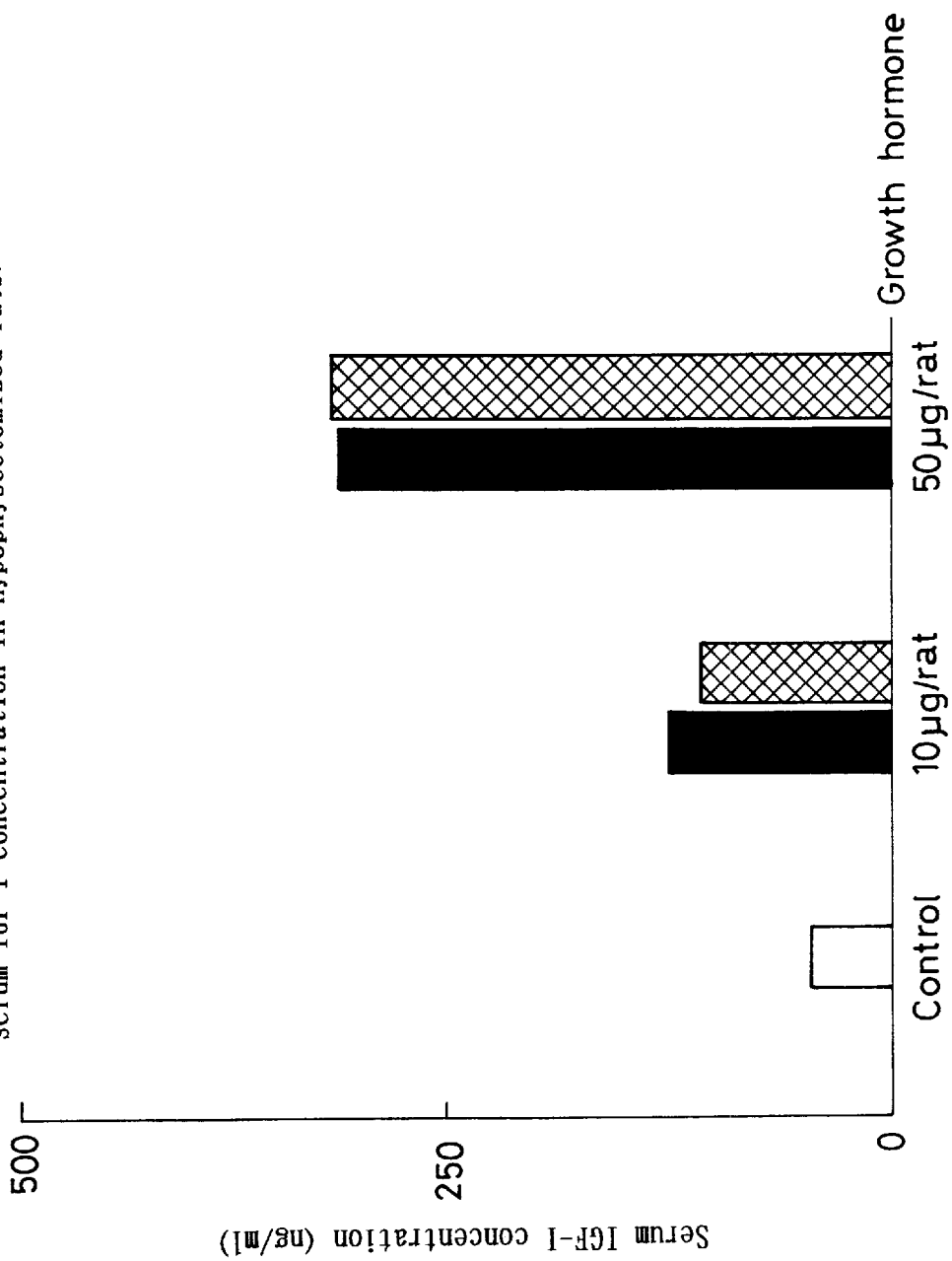
FIG. 5 illustrates a serum IGF-I concentration increasing activity of human growth hormones in hypophysectomized rats. Open column: without growth hormones; crisscross-patterned column: with 22-kilodalton human growth hormone; and solid column: with authentic 20-kilodalton human growth hormone.

Results are shown in FIG. 5. The increase in serum IGF-I level with the administration of the authentic 20-kilodalton human growth hormone was equal to that with the administration of 22-kilodalton human growth hormone. Thus, it was demonstrated that the authentic 20-kilodalton human growth hormone has a serum IGF-I concentration increasing activity, which is necessary for the replacement therapy for adults, particularly growth hormone-deficient adult patients.

Example 8

Study on Glucose Tolerance of Authentic 20-kilodalton Human Growth Hormone in C57BL/6J-ob/ob Mice 6-week-old female C57BL/6J-ob/ob mice were subcutaneously injected in the back with the authentic 20-kilodalton human growth hormone produced in Example 1 or the 22-kilodalton human growth hormone (Genotropin, Sumitomo Pharmaceuticals Co., Ltd.) at a dosage of 500 μg/mouse/day for 3 or 10 days. Saline was administered to control animals. On the day following the last administration of the growth hormones (or saline), 2 μg of dexamethasone-21-phosphate was injected subcutaneously in the back. After fasted for 6 hours, the mice were injected intraperitoneally with glucose (1 g/kg body weight). Blood was taken from the orbital plexus just before the injection (0 minute) and, 30, 60 and 90 minutes after the injection of glucose, and the blood glucose level was measured by New Blood Sugar Test (Boehringer Mannheim). The experiment was conducted using 6 mice in each group.

Figure 6A:
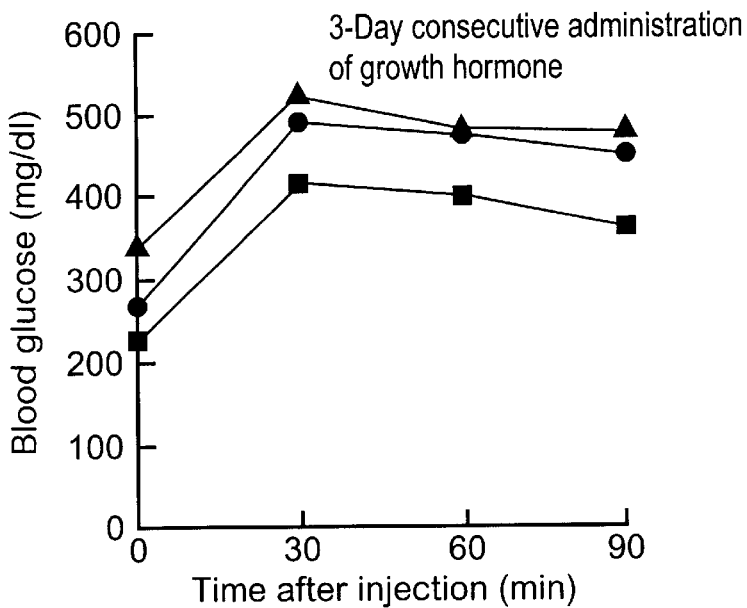
FIG. 6 illustrates glucose tolerance of 20-kilodalton growth hormone and 22-kilodalton growth hormone in C57BL/6J-ob/ob mice. Symbols are ■: control; ▼: with 22-kilodalton human growth hormone; and ●: authentic 20-kilodalton human growth hormone.
Figure 6B:
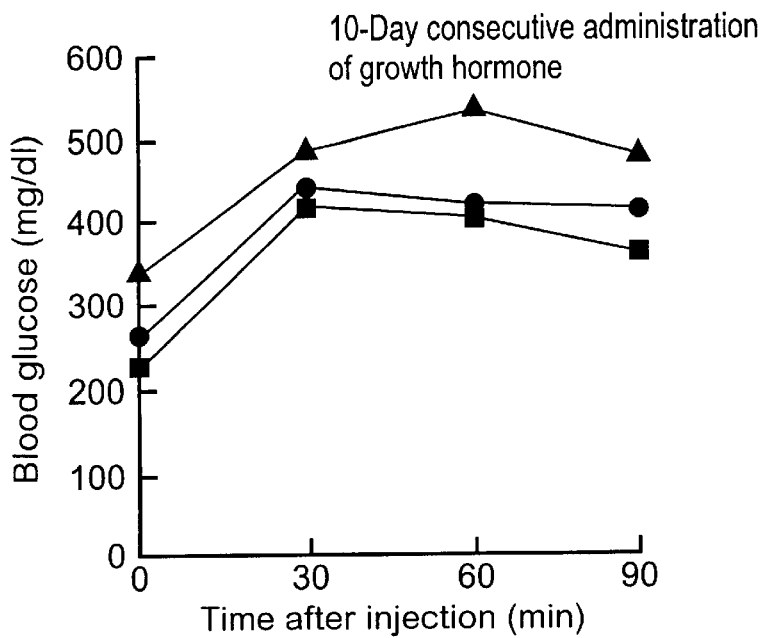

Results are shown in FIG. 6. With administration of the 22-kilodalton human growth hormone, glucose in tolerance was observed; that is, the blood glucose level after the glucose injection was maintained higher than those of control animals. Conversely, when the authentic 20-kilodalton human growth hormone was administered, the blood glucose level 30 minutes after the glucose injection was of the same level as in the control animals, thus indicating no glucose in tolerance. Furthermore, the fasting blood glucose concentration was normal with the administration of 20-kilodalton human growth hormone, while an increase in blood glucose level was already observed at this point with the administration of 22-kilodalton human growth hormone.

These results demonstrated that the 22-kilodalton human growth hormone is diabetogenic, while the 20-kilodalton human growth hormone is not diabetogenic.

---

What is claimed is:

1. A growth hormone replacement therapy comprising administration of an effective amount of a recombinant 20-kilodalton human growth hormone having the amino acid sequence of SEQ ID NO: 1 or 2 to a human growth hormone-deficient patient, wherein the in vivo effect of the lipolysis stimulating activity of said recombinant 20-kilodalton human growth hormone is at least equivalent to the same amount of 22-kilodalton human growth hormone.

2. The growth hormone replacement therapy of claim 1, wherein said recombinant 20-kilodalton human growth hormone has an in vivo effect of the lipolysis stimulating activity and an in vivo body fat reduction activity that are each at least equivalent to the same amount of the 22-kilodalton human growth hormone.

3. The growth hormone replacement therapy of claim 1, wherein said recombinant 20-kilodalton human growth hormone has an in vivo effect of the activity of inducing glucose intolerance that is lower than that of said 22-kilodalton human growth hormone in the same amount.

4. The growth hormone replacement therapy of claim 2, wherein said recombinant 20-kilodalton human growth hormone has an in vivo effect of the activity of inducing glucose intolerance that is lower than that of said 22-kilodalton human growth hormone in the same amount.

5. A method for the improvement of body composition in a human subject, comprising administration of an effective amount of a recombinant 20-kilodalton human growth hormone having the amino acid sequence of SEQ ID NO: 1 or 2 to said human subject, wherein the in vivo effect of the lipolysis stimulating activity of said recombinant 20-kilodalton human growth hormone is at least equivalent to the same amount of 22-kilodalton human growth hormone.

6. A method according to claim 5, wherein the said human subject is a growth hormone-deficient human subject.

7. A method according to claim 5, wherein the authentic 20-kilodalton human growth hormone has an amino acid sequence SEQ ID NO: 1 or SEQ ID NO: 2.

8. A method according to claim 6, wherein the authentic 20-kilodalton human growth hormone has an amino acid sequence SEQ ID NO: 1 or SEQ ID NO: 2.

9. The method of claim 5, wherein said human subject is an adult.

10. The method of claim 6, wherein the human treated is a human adult.

11. The method of claim 5, wherein said recombinant 20-kilodalton human growth hormone has an in vivo effect of the lipolysis stimulating activity and an in vivo body fat reduction activity that are each at least equivalent to the same amount of the 22-kilodalton human growth hormone.

12. The method of claim 5, wherein said recombinant 20-kilodalton human growth hormone has an in vivo effect of the activity of inducing glucose intolerance that is lower than that of said 22-kilodalton human growth hormone in the same amount.

13. The method of claim 11, wherein said recombinant 20-kilodalton human growth hormone has an in vivo effect of the activity of inducing glucose intolerance that is lower than that of said 22-kilodalton human growth hormone in the same amount.

14. A method for lipolysis stimulation in a human subject, comprising administration of an effective amount of a recombinant 20-kilodalton human growth hormone having the amino acid sequence of SEQ ID NO: 1 or 2 to said human subject, wherein the in vivo effect of the lipolysis stimulating activity of said recombinant 20-kilodalton human growth hormone is at least equivalent to the same amount of 22-kilodalton human growth hormone.

15. A method according to claim 14, wherein said human subject is a growth hormone-deficient human subject.

16. A method according to claim 14, wherein the authentic 20-kilodalton human growth hormone has an amino acid sequence SEQ ID NO: 1 or SEQ ID NO: 2.

17. A method according to claim 15, wherein the authentic 20-kilodalton human growth hormone has an amino acid sequence SEQ ID NO: 1 or SEQ ID NO: 2.

18. The method of claim 14, wherein the human subject is a human adult.

19. The method of claim 15, wherein the human subject is a human adult.

20. The method of claim 14, wherein said recombinant 20-kilodalton human growth hormone has an in vivo effect of the lipolysis stimulating activity and an in vivo body fat reduction activity that are each at least equivalent to the same amount of the 22-kilodalton human growth hormone.

21. The method of claim 14, wherein said recombinant 20-kilodalton human growth hormone has an in vivo effect of the activity of inducing glucose intolerance that is lower than that of said 22-kilodalton human growth hormone in the same amount.

22. The method of claim 20, wherein said recombinant 20-kilodalton human growth hormone has an in vivo effect of the activity of inducing glucose intolerance that is lower than that of said 22-kilodalton human growth hormone in the same amount.

23. A method for increasing serum insulin-like growth factor I in a human subject, comprising administration of an effective amount of a recombinant 20-kilodalton human growth hormone having the amino acid sequence of SEQ ID NO: 1 or 2, wherein the in vivo effect of the lipolysis stimulating activity of said recombinant 20-kilodalton human growth hormone is at least equivalent to the same amount of 22-kilodalton human growth hormone.

24. A method according to claim 23, wherein the said human subject is a growth hormone-deficient human subject.

25. A method according to claim 23, wherein the authentic 20-kilodalton human growth hormone has an amino acid sequence SEQ ID NO: 1 or SEQ ID NO: 2.

26. A method according to claim 24, wherein the authentic 20-kilodalton human growth hormone has an amino acid sequence SEQ ID NO: 1 or SEQ ID NO: 2.

27. The method of claim 23, wherein the human subject is a human adult.

28. The method of claim 24, wherein the human subject is a human adult.

29. The method of claim 23, wherein said recombinant 20-kilodalton human growth hormone has an in vivo effect of the lipolysis stimulating activity and an in vivo body fat reduction activity that are each at least equivalent to the same amount of the 22-kilodalton human growth hormone.

30. The method of claim 23, wherein said recombinant 20-kilodalton human growth hormone has an in vivo effect of the activity of inducing glucose intolerance that is lower than that of said 22-kilodalton human growth hormone in the same amount.

31. The method of claim 29, wherein said recombinant 20-kilodalton human growth hormone has an in vivo effect of the activity of inducing glucose intolerance that is lower than that of said 22-kilodalton human growth hormone in the same amount.

\* \* \* \* \*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 176 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Phe Pro Thr Ile Pro Leu Ser Arg Leu Phe A sp Asn Ala Met Leu Arg
1               5                   10                  15

Ala His Arg Leu His Gln Leu Ala Phe Asp T hr Tyr Gln Glu Phe Asn
                20                  25                  30

Pro Gln Thr Ser Leu Cys Phe Ser Glu Ser I le Pro Thr Pro Ser Asn
            35                  40                  45

Arg Glu Glu Thr Gln Gln Lys Ser Asn Leu G lu Leu Arg Ile Ser
        50                  55                  60

Leu Leu Leu Ile Gln Ser Trp Leu Glu Pro V al Gln Phe Leu Arg Ser
65                  70                  75                  80

Val Phe Ala Asn Ser Leu Val Tyr Gly Ala S er Asp Ser Asn Val Tyr
                85                  90                  95

Asp Leu Leu Lys Asp Leu Glu Glu Gly Ile G ln Thr Leu Met Gly Arg
                100                 105                 110

Leu Glu Asp Gly Ser Pro Arg Thr Gly Gln I le Phe Lys Gln Thr Tyr
            115                 120                 125

Ser Lys Phe Asp Thr Asn Ser His Asn Asp A sp Ala Leu Leu Lys Asn
        130                 135                 140

Tyr Gly Leu Leu Tyr Cys Phe Arg Lys Asp M et Asp Lys Val Glu Thr
145                 150                 155                 160

Phe Leu Arg Ile Val Gln Cys Arg Ser Val G lu Gly Ser Cys Gly Phe
                165                 170                 175
```

(2) INFORMATION FOR SEQ ID NO:2:

(i) SEQUENCE CHARACTERISTICS:
      (A) LENGTH: 176 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:2:

```
Phe Pro Thr Ile Pro Leu Ser Arg Leu Phe A sp Asn Ala Ser Leu Arg
1               5                   10                  15

Ala His Arg Leu His Gln Leu Ala Phe Asp T hr Tyr Gln Glu Phe Asn
                20                  25                  30

Pro Gln Thr Ser Leu Cys Phe Ser Glu Ser I le Pro Thr Pro Ser Asn
            35                  40                  45
```

```
Arg Glu Glu Thr Gln Gln Lys Ser Asn Leu Glu Leu Leu Arg Ile Ser
    50                  55                  60

Leu Leu Leu Ile Gln Ser Trp Leu Glu Pro Val Gln Phe Leu Arg Ser
65              70                  75                  80

Val Phe Ala Asn Ser Leu Val Tyr Gly Ala Ser Asp Ser Asn Val Tyr
            85                  90                  95

Asp Leu Leu Lys Asp Leu Glu Glu Gly Ile Gln Thr Leu Met Gly Arg
            100                 105                 110

Leu Glu Asp Gly Ser Pro Arg Thr Gly Gln Ile Phe Lys Gln Thr Tyr
        115                 120                 125

Ser Lys Phe Asp Thr Asn Ser His Asn Asp Asp Ala Leu Leu Lys Asn
    130                 135                 140

Tyr Gly Leu Leu Tyr Cys Phe Arg Lys Asp Met Asp Lys Val Glu Thr
145             150                 155                 160

Phe Leu Arg Ile Val Gln Cys Arg Ser Val Glu Gly Ser Cys Gly Phe
            165                 170                 175
```